United States Patent [19]

Tao et al.

[11] Patent Number: 4,921,947

[45] Date of Patent: May 1, 1990

[54] PROCESS FOR PREPARING MACROLIDE DERIVATIVES

[75] Inventors: Eddie V. P. Tao; Jeffrey T. Vicenzi, both of Indianapolis, Ind.

[73] Assignee: Eli Lilly and Company, Indianapolis, Ind.

[21] Appl. No.: 846,446

[22] Filed: Mar. 31, 1986

[51] Int. Cl.$^5$ .............................................. C07M 1/00
[52] U.S. Cl. ...................................... 536/7.1; 536/124
[58] Field of Search ................................. 536/7.1, 124

[56] References Cited

U.S. PATENT DOCUMENTS

| | | | |
|---|---|---|---|
| 4,440,759 | 4/1984 | Omura et al. | 424/180 |
| 4,443,436 | 4/1984 | Kirst et al. | 424/180 |
| 4,454,314 | 6/1984 | Nagel | 536/7.1 |
| 4,468,511 | 8/1984 | Kirst et al. | 536/7.1 |
| 4,517,359 | 5/1985 | Kobrehel et al. | 536/7.4 |

OTHER PUBLICATIONS

Matsubara et al., "Chemical Modificatoins of Tylosin: Synthesis of Amino Derivatives of C-20 Position of Tylosin and Demycarosyltylosin," *J. Antibiotics* 36 (12), 1713–1721 (1983).
Omura et al., "Novel Dimeric Derivatives of Leucomycins and Tylosin, Sixteen–Membered Macrolides," *J. Med. Chem.* 25, 271–275 (1982).
DeBenneville et al., "The Behavior of Aliphatic Aldehydes in the Leuckart-Wallach Reaction," *J. Amer. Chem. Soc.* 72, 3073–3075 (1950).
Bach, "Preparation of Tertiary N,N–Dimethylamines by the Leuckart Reaction," *J. Org. Chem.* 33 (4), 1647–1649 (1968).
Davis et al., "Steroid Amines. Part V. 20-Pyrrolidin-1-ylpregnane Derivatives," *J. Chem. Soc. Perkin I* 1972, 1420–1424.
Debono et al., *Chem. Abstr.* 101(13):111343n, Abstract of European Patent Appln. EP103465A1, Mar. 21, 1984.
Debono et al., Chem. Abstr. 102(13):113885k, Abstract of U.K. Patent Appln. GB2,135,670A1, Sep. 5, 1984.
"Weygand/Hilgetag Preparative Organic Chemistry", G. Hilgetag and A, Martini, Eds, John Wiley and Sons, New York, 1972, pp. 524–527.

*Primary Examiner*—Herbert J. Lilling
*Assistant Examiner*—Elli Peselev
*Attorney, Agent, or Firm*—Nancy J. Harrison; Leroy Whitaker

[57] ABSTRACT

This invention provides an improvement in the process for preparing C-20-amino-substituted derivatives of the macrolide antibiotics of the tylosin type by reductively aminating the C-20 aldehyde group in the parent antibiotic. The improvement comprises using formic acid as the reducing agent. The new process is less expensive and more amenable to scale-up than previously used processes, but is still selective.

19 Claims, No Drawings

PROCESS FOR PREPARING MACROLIDE DERIVATIVES

SUMMARY OF THE INVENTION

This invention provides an improved process for preparing certain C-20-amino-substituted macrolide derivatives. These derivatives, which are formed by reductive amination of the C-20 aldehyde group in the parent macrolide, were previously prepared using reducing agents such as sodium borohydride and sodium cyanoborohydride. In the improved process of this invention, formic acid is used as the reducing agent. The new process retains the selectivity achieved with metal cyanoborohydrides, but is safer and more amenable to scale-up to produce commercially useful amounts of the derivatives. Furthermore, the new process is less expensive than the earlier processes, both in terms of cost of materials and in terms of procedures needed for waste treatment.

DETAILED DESCRIPTION OF THE INVENTION

This invention relates to a new process for preparing certain C-20-amino-substituted derivatives of the macrolide antibiotics tylosin, desmycosin, macrocin, lactenocin, 2'''-O-demethylmacrocin (DOMM) and 2''-O-demethyllactenocin (DOML). One group of the derivatives which can be advantageously prepared by this process is described by Omura et al. in U.S. Pat. No. 4,440,759, issued Apr. 3, 1984. Another group of derivatives for which this process is useful is described by Debono et al. in pending U.S. application Ser. No. 645,936, filed Aug. 30, 1984. The C-20-amino-substituted derivatives which can be prepared by the process of this invention have the common general formula:

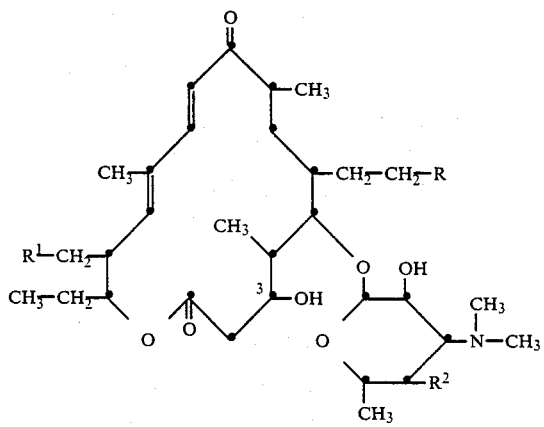

wherein R is a group of formula:

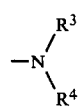

and (i) $R^3$ and $R^4$ independently represent hydrogen, $C_{1-8}$ alkyl, $C_{3-10}$ cycloalkyl, or a $-(CH_2)_n Ph$ group, except that $R^3$ and $R^4$ cannot both be hydrogen;

n is 0, 1 or 2; and

Ph is phenyl optionally substituted by halo, $C_{1-4}$ alkyl or $C_{1-4}$ alkoxy; or (ii) $R^3$ and $R^4$ taken together with the adjacent nitrogen atom, form a monocyclic ring containing from 5 to 12 ring atoms or a bicyclic or tricyclic ring system containing from 8 to 20 ring atoms, wherein one of the other ring atoms can be oxygen, sulfur or nitrogen and one or more of the carbon atoms may be substituted by $C_{1-4}$ alkyl, $C_{2-4}$ alkenyl, $C_{2-4}$ alkynyl, $C_{1-4}$ alkoxy, hydroxyl, halo, halo-$C_{1-4}$ alkyl, $-N(C_{1-4}$ alkyl$)_2$, $-N(CH_2)_m$,

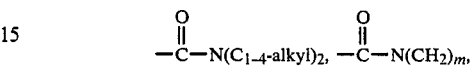

cyano, ethylenedioxy, benzyl, phenyl, or phenyl substituted by from 1 to 3 substituents selected from halo, $C_{1-4}$-alkyl or $C_{1-4}$ alkoxy;

m is an integer from 4 through 7;

$R^1$ is

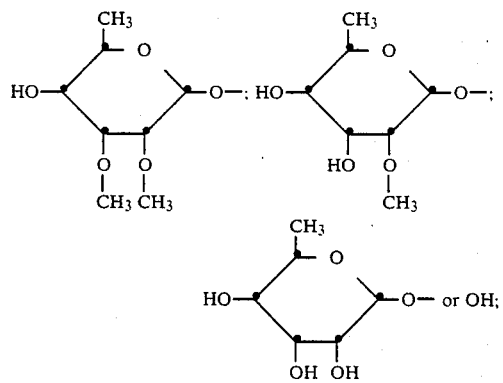

$R^2$ is hydrogen, hydroxyl or

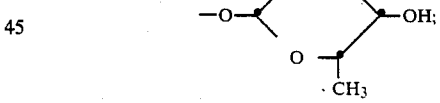

(mycarosyloxy)

and the acid addition salts of these compounds.

Although no stereochemical assignments are indicated in the structures given herein, the stereochemistry is identical to that of the antibiotics from which the compounds are prepared, e.g. tylosin.

The subgroup of formula 1 compounds wherein $R^3$ and $R^4$ taken together with the adjacent nitrogen atom form a monocyclic ring is an especially useful group.

Representative monocyclic rings are pyrrolidin-1-yl, piperidin-1-yl, morpholin-4-yl, piperazin-1-yl, hexahydroazepin-1-yl, octahydroazocin-1-yl, octahydro-1H-azonin-1-yl, azacyclotridecan-1-yl and the like.

Representative bicyclic and tricyclic rings are decahydroquinolin-1-yl; decahydroisoquinolin-2-yl; decahydrocyclohepta[b]pyrrol-1-yl; decahydrocyclohepta[c]pyrrol-2-yl; decahydrocyclopent[c]azepin-2-yl; decahydrocyclopent[d]azepin-3-yl; an azabicycloheptanyl group such as 3-azabicyclo[3.2.0]heptan- 3-yl; an azabicyclooctanyl group such as 6-azabicyclo[3.2.1]octan-6-yl; an azabicyclononanyl group such as 3-azabicyclo[3.2.2]nonan-3-yl; an azabicyclodecanyl group such as 4-azabicyclo[5.3.0]decan-4-yl; an azatricyclogroup such as 2-azatricyclo[6.2.2.2$^{3,6}$]tetradecan-2-yl or dodecahydrocarbazol-9-yl; and a spiro-fused system such as 1-azaspiro[4.5]decan-1-yl.

Representative rings which have one or more substituents on the carbon atoms are 1,3,3-trimethyl-6-azabicyclo[3.2.1]octan-6-yl; 4-piperidinopiperidin-1-yl; 3,3,5-trimethylhexahydroazepin-1-yl; 4-phenylpiperidin-1-yl; 3,5-dimethylpiperidin-1-yl; 3-(N,N-diethylcarbamoyl)-piperidin-1-yl; and the like.

Alkyl groups contain the specified number of carbon atoms and can be straight, branched, or cyclic. Alkenyl and alkynyl groups are hydrocarbon groups containing a double or triple bond, respectively.

Halo substituents are selected from the group consisting of Cl, Br and F.

Omura et al. and Debono et al. prepared the formula 1 compounds by reductive amination of an aldehyde of formula 2.

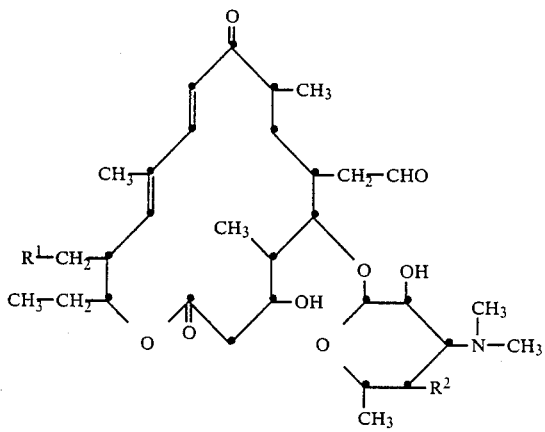

2 wherein R$^1$ and R$^2$ are as previously defined, using an amine of formula 3:

3 wherein R$^3$ and R$^4$ are as previously defined, and a reducing agent selected from a (group IA metal or ammonium) cyanoborohydride or borohydride. Metal cyanoborohydrides were preferred over metal borohydrides for this reaction because they are more selective. Their use minimized reducing either the dienone in the macrolide ring or the C-20 aldehyde to the alcohol. Metal cyanoborohydrides, however, are expensive and are not readily available in very large quantities. In addition, use of cyanoborohydrides may liberate cyanide, a very toxic material, during the reaction. Thus, its use in large-scale processes would cause waste disposal problems.

We have discovered that the reductive amination of macrolides can be achieved by using formic acid as the reducing agent. This discovery provides an improved process for preparing the formula 1 compounds by reductively aminating the corresponding formula 2 compounds. Use of formic acid provides efficient reductive amination without altering the remainder of the macrolide, which includes a number of sensitive sites, such as a carbonyl group at C-9, double bonds, the aldehyde at C-20, sugar groups and the lactone and the possibility of dehydration at C-3. In addition, formic acid is less expensive than the metal cyanohydrides or hydrides. Furthermore, it is more readily available in large quantities than the cyanohydrides or hydrides. Thus, its use makes production of commercial amounts of the formula 1 compounds more feasible. Another advantage of formic acid is that it does not pose the waste removal problems encountered when using cyanoborohydrides.

The solvent used in the process of this invention will ordinarily be an inert, polar organic solvent such as, for example, amyl acetate or acetonitrile.

Typical temperatures for this process will vary from about 35° C. to about 80° C., with temperatures of from about 60° C. to about 75° C. being preferred.

The concentration of the formic acid solution which is used is not limiting; however, concentrations above 90% formic acid are preferred and concentrations above 95% are especially preferred. From about one to about two equivalents of formic acid should be used in this process. Slightly more than one equivalent of formic acid is a preferred amount.

The process is carried out until the amination is complete. The time required for completion will vary, depending upon a variety of factors, such as temperature, the aminating agent being used, etc. The progress of the process can be monitored using standard techniques, such as high performance liquid chromatography (HPLC) and thin-layer chromatography (TLC).

To further illustrate the process of this invention, the following non-limiting examples are provided. In these examples, the abbreviation "20-DH-DO" is used for the term "20-dihydro-20-deoxy".

EXAMPLE 1

Preparation of
20-DH-DO-20-(3,5-dimethylpiperidin-1-yl)desmycosin

Desmycosin (15.44 g, 0.02 mole), 3,5-dimethylpiperidine (2.26 mL), acetonitrile (80 mL) and K$_2$CO$_3$ (2.76 g) were mixed and stirred for one hour at room temperature. The K$_2$CO$_3$ was removed by filtration. A mixture of acetonitrile (20 mL) and 95–97% formic acid (0.917 g, 0.021 mole) was added dropwise to the remaining solution. This mixture was heated to about 65° C. until the gas evolution which occurred had stopped. The reaction mixture was cooled, and the pH of the solution was adjusted to 6.5. The precipitate which formed was separated by filtration and then dissolved in water (400 mL). The pH of this solution was adjusted to 11–12. The mixture was stirred, and the precipitate which formed was filtered, washed with water and dried in a vacuum oven at about 60° C. to give 12.64 g (90% yield) of the title compound.

EXAMPLE 2

Alternate Preparation of
20-DH-DO-20-(3,5-dimethylpiperidin-1-yl)desmycosin

Dichloromethane (40 mL), 95–97% formic acid (1.97 g, 0.04 mole) and 3,5-dimethylpiperidine free base (2.76 mL) were mixed together and heated to reflux. A solution of desmycosin (15.44 g) in CH$_2$Cl$_2$ (60 mL) was added dropwise into the refluxing reaction mixture over about one hour at a temperature of 42° C. After about 1.5 hours, water (100 mL) was added. The pH, which was about 5.9, was adjusted to 4.3 by the addition of concentrated HCl. Water (300 mL) was added to the separated aqueous layer, and the pH of this solution was adjusted to 11 with 20% sodium hydroxide. The solids which precipitated upon pH adjustment were separated by filtration, washed with water and dried to give 14.6 g of product (92.3% yield).

EXAMPLE 3

Preparation of 20-DH-DO-20-(3,5-dimethylpiperidin-1-yl)desmycosin from Tylosin

Tylosin phosphate in water (399 mg/mL, 91.0 mL, 0.04 mole) was slowly heated to 35° C. while adjusting the pH of the solution to 1.6 by the addition of $H_2SO_4$. After being heated for one hour, the reaction mixture was cooled to room temperature. Amyl acetate (80 mL) was added to the mixture, and the pH was adjusted to 11 by the addition of 5N NaOH. The amyl acetate layer was separated. 3,5-Dimethylpiperidine (4.52 g, 0.04 mole) was added to the amyl acetate solution at room temperature, and the reaction mixture was then heated to 70° C. Formic acid (96%, 2.01 g, 0.042 mole) in amyl acetate (20 mL) was added slowly to the amyl acetate solution. After two hours, the reaction mixture was cooled to room temperature. Water (100 mL) was added, and the pH of this solution was adjusted to about 4.5 by the addition of concentrated HCl. The aqueous layer was separated and diluted with water (700 mL). This solution was stirred at room temperature as its pH was raised to about 11 by the addition of 5N NaOH. The white precipitate which formed was separated by filtration and dried under vacuum to give 28.86 g of the product (87.3% yield).

EXAMPLE 4

Preparation of 20-DH-DO-20-(3,5-dimethylpiperidin-1-yl)tylosin and 20-DH-DO-20-(3,5-dimethylpiperidin-1-yl)desmycosin Amyl acetate (100 mL) was added to tylosin phosphate in water (91.0 mL, 399 mg/mL). The pH of this solution was adjusted to 11 with 5N NaOH. The organic layer was separated. 3,5-Dimethylpiperidine (4.52 g) was added to this solution, and the reaction mixture was heated to 70° C. Formic acid (96%, 1.96 g) in amyl acetate (30 mL) was added to this mixture over a period of 20 minutes, and the reaction mixture was allowed to stir overnight at 70° C. Water (60 mL) was then added, and the pH of the solution was adjusted to 3.0. The organic layer was separated and discarded. The aqueous layer, which contained 20-DH-DO-20-(3,5-dimethylpiperidin-1-yl)tylosin was adjusted to pH 1.5–1.6 with 60% $H_2SO_4$. Hydrolysis was complete in 1.5 hours. Water (600 mL) was then added, and the pH of the solution was adjusted to 11 with 5N NaOH. The white precipitate which formed was separated by filtration, washed with water (120 mL) and dried to give 25.09 g of 20-DH-DO-20-(3,5-dimethylpiperidin-1-yl)desmycosin (77% yield).

EXAMPLE 5

Preparation of 20-(di-n-Propylamino)desmycosin from Tylosin

The pH of a solution of tylosin phosphate in water (369 mg/mL, 100 mL, 0.04 mole) was adjusted to 1.6 wth 60% $H_2SO_4$ (2.2 mL). The resulting solution was heated to 35°–40° C. for 1.75 hr.; at this point, HPLC indicated that hydrolysis was complete.

Amyl acetate (80 mL) was added to this solution, and the pH of the mixture was adjusted to 11 with 5N NaOH (25 mL). The amyl acetate layer was separated and filtered through $MgSO_4$. (di-n-Propyl)amine (4.08 g, 0.04 mole) was added, and the resulting solution was heated to 70° C. A solution containing amyl acetate (10 mL) and formic acid (2 g) was added, and the reaction mixture was heated at 70° C. for 20 hours. After the reaction mixture had cooled to room temperature, water (100 mL) was added and the pH was adjusted to 4.1 with 60% $H_2SO_4$. The amyl acetate layer was separated and extracted with water (100 mL). The combined aqueous layers were diluted with water (600 mL), and the pH of the solution was adjusted to 11 with 5N NaOH. The resulting precipitate was separated by filtration, washed with water and vacuum-dried at 40° C. to give 24.1 g (64% yield) of the title compound: UV max (EtOH) 283 nm ($\epsilon$ 24,988); FDMS: $M^+ = 856$.

EXAMPLE 6

Preparation of 20-DH-DO-20-(di-isobutylamino)desmycosin

Using a procedure like that described in Example 5, tylosin (369 mg/mL, 100 mL, 0.04 mole) was hydrolyzed to desmycosin. The resulting desmycosin in amyl acetate (67 mL) and diisobutylamine (2.6 g, 0.02 mole) were heated to 70° C. A solution containing amyl acetate (5 mL) and formic acid (1 g) was added dropwise. The resulting solution was heated at 70° C. for 21 hours and then cooled to room temperature. Water (100 mL) was added, and the pH of the mixture was adjusted to 4.1 with 60% $H_2SO_4$. The aqueous layer was separated and diluted with water (300 mL). The pH of the resulting solution was adjusted to 11 with 5N NaOH. The precipitate which formed was removed by filtration, washed with water and vacuum-dried at 40° to give 15.8 g (80.3% yield) of the title compound: UV max (EtOH) 281 nm ($\epsilon$ 23,105); FDMS: $M^+ = 885$.

EXAMPLE 7

Preparation of 20-DH-DO-20-(3-azabicyclo[3.2.2]nonan-3-yl)desmycosin

Desmycosin in amyl acetate, prepared as in Example 5 (67 mL) and 3-azabicyclo[3.2.2]nonane (2.5 g 0.02 mole) were heated to 70° C. A solution containing amyl acetate (5 mL) and formic acid (1 g) was added dropwise. The resulting solution was heated at 70° C. for 1.33 hr. After the reaction mixture was cooled to room temperature, water (100 mL) was added. The pH of the mixture was adjusted to 4.0 with 60% $H_2SO_4$. The aqueous layer was separated and diluted with water (300 mL). The pH of this solution was adjusted to 11 with 5N NaOH, and the precipitate which formed was removed by filtration, washed with water and vacuum-dried at 40° C. to give 16.2 g (92% yield) of the title compound: UV max (EtOH) 281 nm ($\epsilon$ 22,711); FDMS: $M^+ = 880$.

EXAMPLE 8

Using a procedure like that described in Example 5, tylosin (389 mg/mL, 100 mL~0.04 mole) was hydrolyzed to desmycosin. n-Hexylamine (4.0 g) was added to the resulting desmycosin in amyl acetate, and the solution was heated to 70° C. A solution containing amyl acetate (10 mL) and formic acid (2 g) was added. The resulting solution was heated at 70° C. for 2 hours and then cooled to room temperature. Water (100 mL) was added, and the pH of the mixture was adjusted to 4.1 with 60% H₂SO₄. The amyl acetate layer was separated and extracted with water (100 mL). The aqueous layer and the water extract were combined and diluted with water (600 mL). The pH of the resulting solution was adjusted to 11 with 5N NaOH (12 mL). The precipitate which formed was removed by filtration, washed with water and vacuum-dried at 40° C. to give a total of 15.1 g of the title compound: UV max (EtOH) 282 nm ($\epsilon$ 17,318); FDMS: M⁺=857; titratable groups at 7.3 and 10 in 66% aqueous DMF.

We claim:

1. In the process for preparing a C-20-amino-substituted derivative of formula 1:

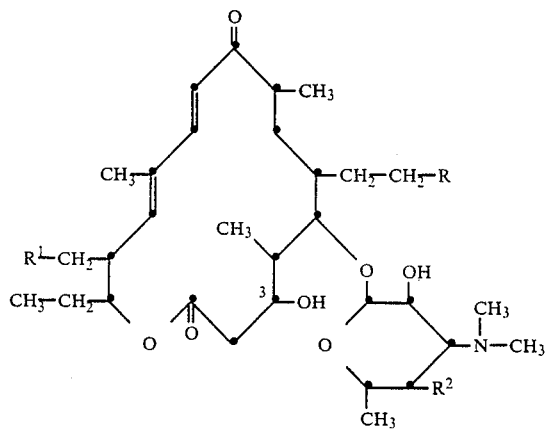

wherein R is a group of formula:

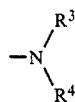

and
(i) R³ and R⁴ independently represent hydrogen, $C_{1-8}$ alkyl, $C_{3-10}$ cycloalkyl, or a —(CH₂)ₙPh group, except that R³ and R⁴ cannot both be hydrogen; n is 0, 1 or 2; and
Ph is phenyl optionally substituted by halo, $C_{1-4}$ alkyl or $C_{1-4}$ alkoxy; or
(ii) R³ and R⁴ taken together with the adjacent nitrogen atom, form a monocyclic ring containing from 5 to 12 ring atoms or a bicyclic or tricyclic ring system containing from 8 to 20 ring atoms, wherein one of the other ring atoms can be oxygen, sulfur or nitrogen and one or more of the carbon atoms may be substituted by $C_{1-4}$ alkyl, $C_{2-4}$ alkenyl, $C_{2-4}$ alkynyl, $C_{1-4}$ alkoxy, hydroxyl, halo, halo-$C_{1-4}$ alkyl, —N($C_{1-4}$ alkyl)₂, —N(CH₂)ₘ,

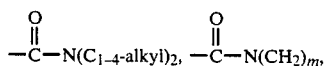

cyano, ethylenedioxy, benzyl, phenyl, or phenyl substituted by from 1 to 3 substituents selected from halo, $C_{1-4}$-alkyl or $C_{1-4}$ alkoxy;
m is an integer from 4 through 7;

R¹ is

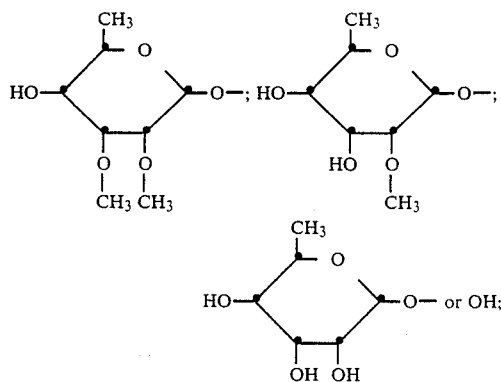

R² is hydrogen, hydroxyl or

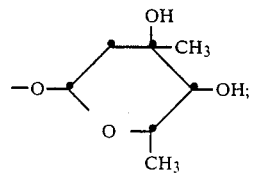

or its acid addition salt, by reductively aminating an aldehyde of formula 2:

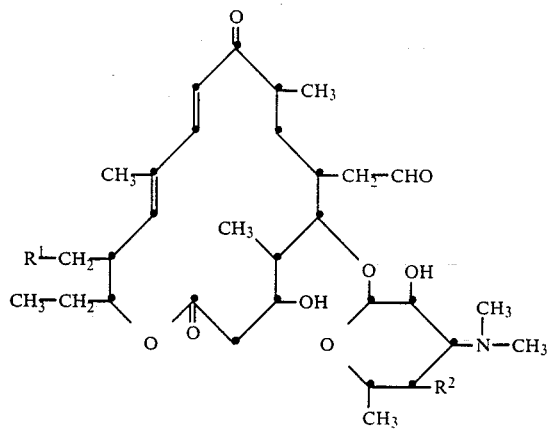

using an aminating agent of formula 3:

wherein R₃ and R₄ are as previously defined and a reducing agent,
the improvement which comprises using from about one to about two equivalents of formic acid as the reducing agent and carrying out the reaction in an inert, polar organic solvent at a temperature of from about 35° to about 80° C.

2. A process of claim 1 wherein R³ and R⁴ taken together with the adjacent nitrogen atom form a monocyclic ring.

3. A process of claim 2 wherein the ring contains from 5 to 8 ring atoms.

4. A process of claim 1 wherein $R^3$ and $R^4$ taken together with the adjacent nitrogen atom form a bicyclic or tricyclic ring system.

5. A process of claim 4 wherein the ring system is bicyclic.

6. A process of claim 4 wherein the ring system is tricyclic.

7. A process of claim 1 wherein the $R^1$ group is

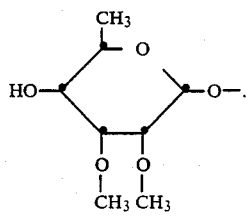

8. A process of claim 7 wherein the $R^2$ group is hydroxy.

9. A process of claim 2 wherein the ring is octahydroazocin-1-yl, hexahydroazepin-1-yl, octahydro-1H-azonin-1-yl, piperidin-1-yl, or 1,2,3,6-tetrahydropyridin-1-yl.

10. The process of claim 9 wherein the formula 1 compound is 20-dihydro-20-deoxy-20-(piperidin-1-yl)desmycosin.

11. The process of claim 9 wherein the ring is substituted.

12. The process of claim 11 wherein the formula 1 compound is 20-dihydro-20-deoxy-20-(3,5-dimethylpiperidin-1-yl)desmycosin.

13. The process of claim 12 wherein the methyl substituents are in the cis configuration.

14. The process of claim 12 wherein the methyl substituents are in the trans configuration.

15. A process of claim 4 wherein the ring is 1,2,3,4-tetrahydroisoquinolin-1-yl; 1-azaspiro[4.5]decan-1-yl; 3-azaspiro[5.5]undecan-3-yl; azabicyclononanyl; decahydroquinolin-1-yl; 1,8,8-trimethyl-3-azabicyclo[3.2.1]octan-3-yl; 1,3,3-trimethyl-6-azabicyclo[3.2.1]octan-6-yl, or dodecahydrocarbazol-9-yl.

16. The process of claim 15 wherein the formula 1 compound is 20-dihydro-20-deoxy-20-[3-azabicyclo[3.2.2]nonan-3-yl]desmycosin.

17. The process of claim 1 wherein the temperature is from about 60° to about 75°.

18. The process of claim 1 wherein the solvent used is selected from amyl acetate and acetonitrile.

19. The process of claim 1 wherein the formic acid used is in a solution having a concentration of greater than 90% formic acid.

* * * * *

UNITED STATES PATENT AND TRADEMARK OFFICE
CERTIFICATE OF CORRECTION

PATENT NO.   :   4,921,947

DATED        :   May 1, 1990

INVENTOR(S)  :   Eddie V. P. Tao *et al*.

It is certified that an error appears in the above-identified patent and that said Letters Patent is hereby corrected as shown below:

```
In column 6 in the line following "EXAMPLE 8", insert

--Preparation of 20-DH-DO-20(n-hexylamino)desmycosin--
```

Signed and Sealed this

Second Day of November, 1993

*Attest:*

BRUCE LEHMAN

*Attesting Officer*    Commissioner of Patents and Trademarks